(12) United States Patent
Avidano et al.

(10) Patent No.: US 11,730,522 B2
(45) Date of Patent: Aug. 22, 2023

(54) THREADED SPINAL ROD REDUCER

(71) Applicant: SPINE WAVE, INC., Shelton, CT (US)

(72) Inventors: Eugene Avidano, Stratford, CT (US);
Dylan Freund, San Marcos, CA (US);
Mark Serokosz, New Fairfield, CT (US)

(73) Assignee: SPINE WAVE, INC., Shelton, CT (US)

( * ) Notice: Subject to any disclaimer, the term of this patent is extended or adjusted under 35 U.S.C. 154(b) by 256 days.

(21) Appl. No.: 17/034,637

(22) Filed: Sep. 28, 2020

(65) Prior Publication Data

US 2021/0059725 A1 Mar. 4, 2021

Related U.S. Application Data

(63) Continuation-in-part of application No. 16/129,957, filed on Sep. 13, 2018, now abandoned.

(60) Provisional application No. 62/575,140, filed on Oct. 20, 2017.

(51) Int. Cl.
*A61B 17/70* (2006.01)
*A61B 17/00* (2006.01)

(52) U.S. Cl.
CPC .............. *A61B 17/7086* (2013.01); *A61B 2017/00424* (2013.01)

(58) Field of Classification Search
CPC ........................ A61B 17/7074–7092
See application file for complete search history.

(56) References Cited

U.S. PATENT DOCUMENTS

| | | | |
|---|---|---|---|
| 5,020,519 | A | 6/1991 | Hayes et al. |
| 5,720,751 | A | 2/1998 | Jackson |
| 5,910,141 | A | 6/1999 | Morrison et al. |
| 6,090,113 | A | 7/2000 | Le Couedic et al. |
| 6,183,472 | B1 | 2/2001 | Lutz |
| 6,660,006 | B2 | 12/2003 | Markworth et al. |
| 7,156,849 | B2 | 1/2007 | Dunbar et al. |
| 7,278,995 | B2 | 10/2007 | Nichols et al. |
| 7,462,182 | B2 | 12/2008 | Lim |
| 7,470,279 | B2 | 12/2008 | Jackson |
| 7,572,281 | B2 | 8/2009 | Runco et al. |
| 7,608,081 | B2 | 10/2009 | Abdelgany |
| 7,621,918 | B2 | 11/2009 | Jackson |

(Continued)

*Primary Examiner* — Eduardo C Robert
*Assistant Examiner* — Steven J Cotroneo
(74) *Attorney, Agent, or Firm* — Hoffmann & Baron, LLP (57) ABSTRACT

A spinal rod reducer for reducing a rod into a rod-receiving opening of a bone anchor comprises an elongate tubular body having a lumen extending therethrough and a pair of spaced flexible anchor attachment members at the distal end of the tubular body. A threaded rod reduction member having a rod contacting surface is supported for axial movement within the lumen. A threaded rotatable reduction knob is threadably engaged with the rod reduction member rotation of which causes the rod reduction member with the rod contacting surface to move axially distally toward the bone anchor. A locking sleeve is configured to axially slide on the tubular body over the attachment members, the locking sleeve including a locking element for releasably coupling the locking sleeve and the rod reduction member for selective independent and joint movement relative to the tubular body.

24 Claims, 8 Drawing Sheets

(56) References Cited

U.S. PATENT DOCUMENTS

| | | | |
|---|---|---|---|
| 7,651,502 B2 | 1/2010 | Jackson | |
| 7,887,539 B2 * | 2/2011 | Dunbar, Jr. | A61B 17/7091 81/452 |
| 7,887,541 B2 | 2/2011 | Runco et al. | |
| 7,931,677 B2 | 4/2011 | Abdelgany | |
| 7,947,046 B2 * | 5/2011 | Justis | A61B 17/88 606/264 |
| 8,142,437 B2 | 3/2012 | McLean et al. | |
| 8,162,948 B2 | 4/2012 | Jackson | |
| 8,172,847 B2 | 5/2012 | Dziedzic et al. | |
| 8,197,519 B2 | 6/2012 | Schlaepfer et al. | |
| 8,303,595 B2 | 11/2012 | Jones | |
| 8,308,729 B2 | 11/2012 | Nunley et al. | |
| 8,439,922 B1 | 5/2013 | Arnold et al. | |
| 8,460,308 B2 | 6/2013 | Marino et al. | |
| 8,540,718 B2 | 9/2013 | Dauster et al. | |
| 8,545,505 B2 * | 10/2013 | Sandstrom | A61B 17/7085 606/86 A |
| 8,556,904 B2 * | 10/2013 | Rezach | A61B 17/7085 606/305 |
| 8,579,943 B2 | 11/2013 | Nichols et al. | |
| 8,636,742 B2 | 1/2014 | Runco et al. | |
| 8,657,825 B2 | 2/2014 | Justis | |
| 8,685,029 B2 | 4/2014 | Dziedzic et al. | |
| 8,961,523 B2 * | 2/2015 | Barrus | A61B 17/7089 606/279 |
| 9,066,761 B2 * | 6/2015 | McBride | A61B 17/7085 |
| 9,192,415 B1 | 11/2015 | Arnold et al. | |
| 9,198,692 B1 | 12/2015 | Doose et al. | |
| 9,198,698 B1 | 12/2015 | Doose et al. | |
| 9,204,909 B2 * | 12/2015 | Rezach | A61B 17/7076 |
| 9,247,969 B2 | 2/2016 | Nunley et al. | |
| 9,265,533 B2 * | 2/2016 | Nelson | A61B 17/7085 |
| 9,271,768 B2 * | 3/2016 | Artaki | A61B 17/7086 |
| 9,452,000 B2 | 9/2016 | Barrus | |
| 9,486,256 B1 | 11/2016 | Lish et al. | |
| 9,532,816 B2 | 1/2017 | Barrus et al. | |
| 9,655,664 B2 | 5/2017 | Barrus et al. | |
| 2008/0243190 A1 * | 10/2008 | Dziedzic | A61B 17/7091 606/264 |
| 2009/0082775 A1 * | 3/2009 | Altarac | A61B 17/025 606/301 |
| 2009/0143828 A1 * | 6/2009 | Stad | A61B 17/7085 606/86 A |
| 2010/0292742 A1 * | 11/2010 | Stad | A61B 17/7091 606/279 |
| 2014/0148865 A1 * | 5/2014 | Hennard | A61B 17/7086 606/86 A |
| 2019/0117280 A1 | 4/2019 | Avidano et al. | |

* cited by examiner

FIG. 3

THREADED SPINAL ROD REDUCER

CROSS-REFERENCES TO RELATED APPLICATIONS

This application is a continuation-in-part application of U.S. application Ser. No. 16/129,957, filed Sep. 13, 2018, now pending, which claims the benefit of U.S. Provisional Patent Application No. 62/575,140, filed Oct. 20, 2017, each of which is incorporated herein by reference in its entirety.

FIELD OF THE INVENTION

The subject invention relates generally to the field of spinal surgery instruments, and more particularly to a threaded rod reducer for reducing a spinal fixation rod into a bone anchor.

BACKGROUND OF THE INVENTION

Techniques and systems have been developed for correcting and stabilizing injuries to or malformation of the spine. In one type of system, an elongated member such as a bendable spinal fixation rod is disposed longitudinally along a length of the spine, spanning two or more vertebral levels. In certain applications, the rod is bent to correspond to the normal curvature of the spine in the particular region being instrumented, such as the normal kyphotic curvature of the thoracic region or the lordotic curvature of the lumbar region. In accordance with such a system, the rod is engaged to various vertebrae along a length of the spinal column by way of a number of anchor devices that utilize a variety of fixation elements configured to engage specific portions of the vertebra and other bones. For instance, one such fixation element is a hook that is configured to engage the laminae of the vertebra. Another very prevalent fixation element is a pedicle screw that can be threaded into various parts of the vertebrae or other bones. Such pedicle screws may be monoaxial or polyaxial, such as the multi-axial screws disclosed in commonly assigned U.S. Pat. No. 8,162,898, entitled "Multi-Axial Fixation Assembly", issued to Potash et al. on Apr. 24, 2012, the disclosure of which is incorporated herein by reference.

Once bone anchors, such as pedicle screws are anchored in the vertebrae, a connecting rod must be nestled or seated within a rod-receiving opening or the slot of each pedicle screw. This approach is often challenging in part because the rod introduction site is not readily visible or because there are no suitable tactile indicators that the rod is properly seated in every bone screw assembly. In order to ensure proper placement of the rod, a rod reducer or persuader may be mounted on one or more of the pedicle screws to provide a sufficient force to the rod to properly and fully urge the rod into the rod-receiving opening.

There are a variety of known rod reduction instruments that are used by surgeons to provide the desired forces required to appropriately reduce spinal fixation rods into bone anchors during surgical procedures. Nevertheless, there is interest in a rod reducer that has features that are simple and easy to use and that may result in less time for the surgeon to complete the rod reduction procedure.

SUMMARY OF THE INVENTION

It is an object of the invention to provide an improved rod reducer for use during surgery, such as spinal surgery. It is a more particular object of the invention to provide a threaded rod reducer that allows the user to reduce spinal fixation rods into bone anchors, such as pedicle screws, in a simple, less time-consuming procedure.

DESCRIPTION OF THE FIGURES

FIG. 9 is an exploded view of the rod reducer of FIG. 7.

DESCRIPTION OF THE EMBODIMENTS

For the purposes of promoting and understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Traditional polyaxial pedicle screws comprise an elongate shaft threaded at one end and a head, typically having a spherical surface, at the other end. A yoke having a U-shaped opening for receiving a spinal fixation rod is typically pre-assembled to the screw head in a manner to allow articulating movement of the yoke relative to the threaded shaft. In a modular pedicle screw construction, the yoke is configured to be articulatingly attached to the screw head subsequent to the threaded installation of the threaded shaft into a pedicle. The rod reducer of the subject invention is applicable for use with both a traditional polyaxial pedicle screw after threaded installation into a pedicle or with a modular polyaxial pedicle screw after in situ attachment of the yoke to the pedicle screw head.

Figure 1:
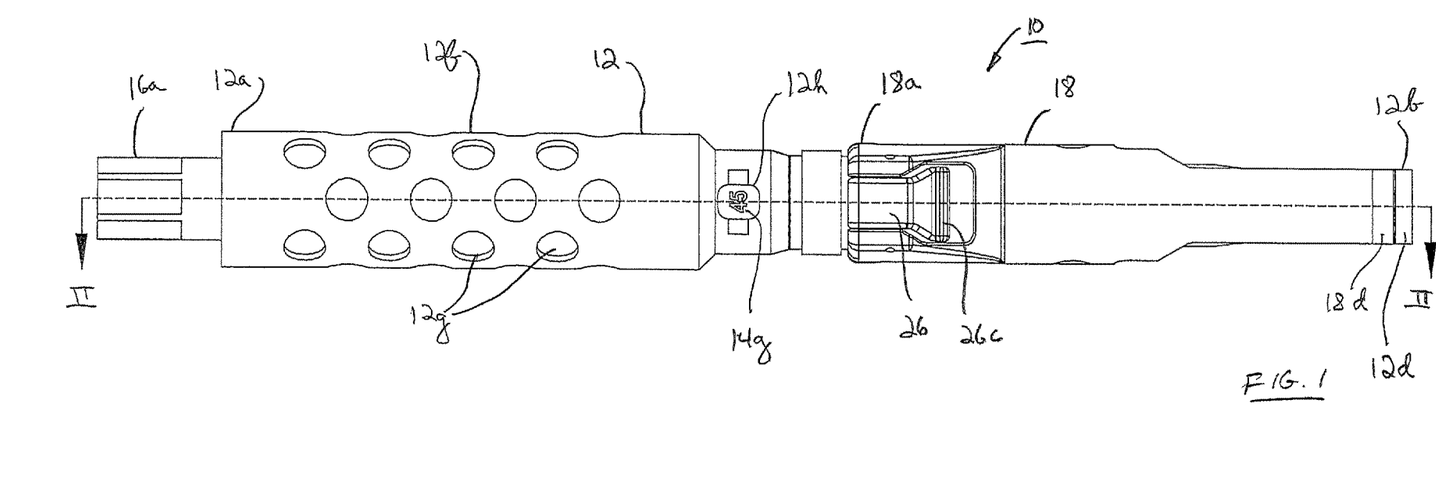
FIG. 1 is a side elevation view of a threaded rod reducer for use during spinal surgery in accordance with a first embodiment of the present invention.
Figure 2:
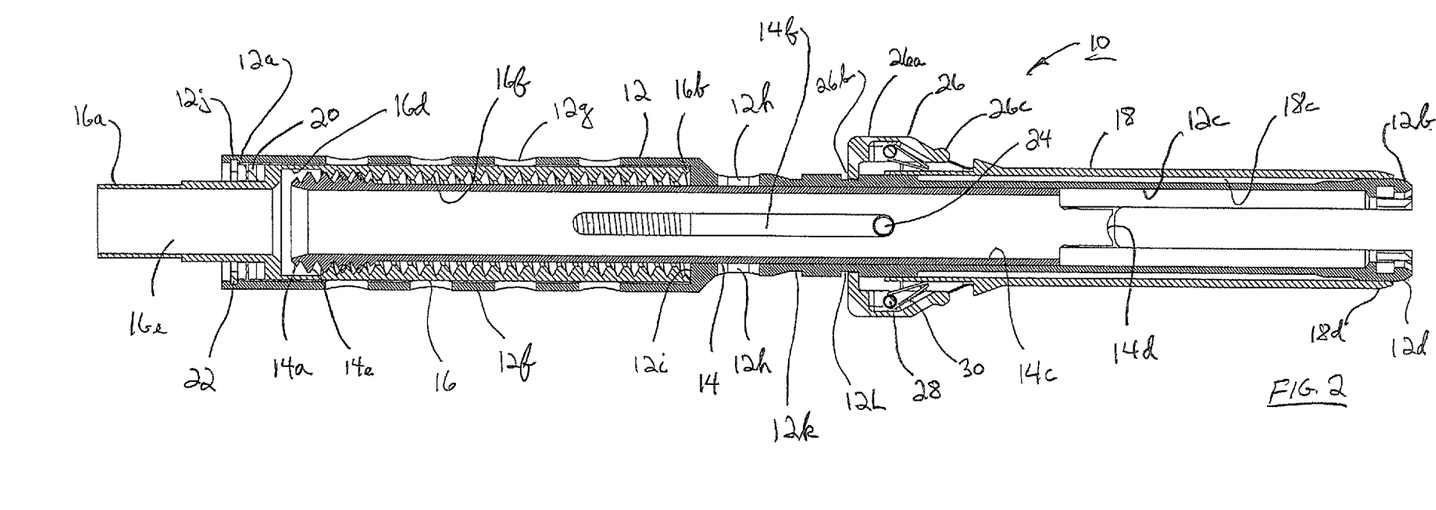
FIG. 2 is a longitudinal cross-sectional view of the rod reducer as seen along viewing lines II-II of FIG. 1.
Figure 3:
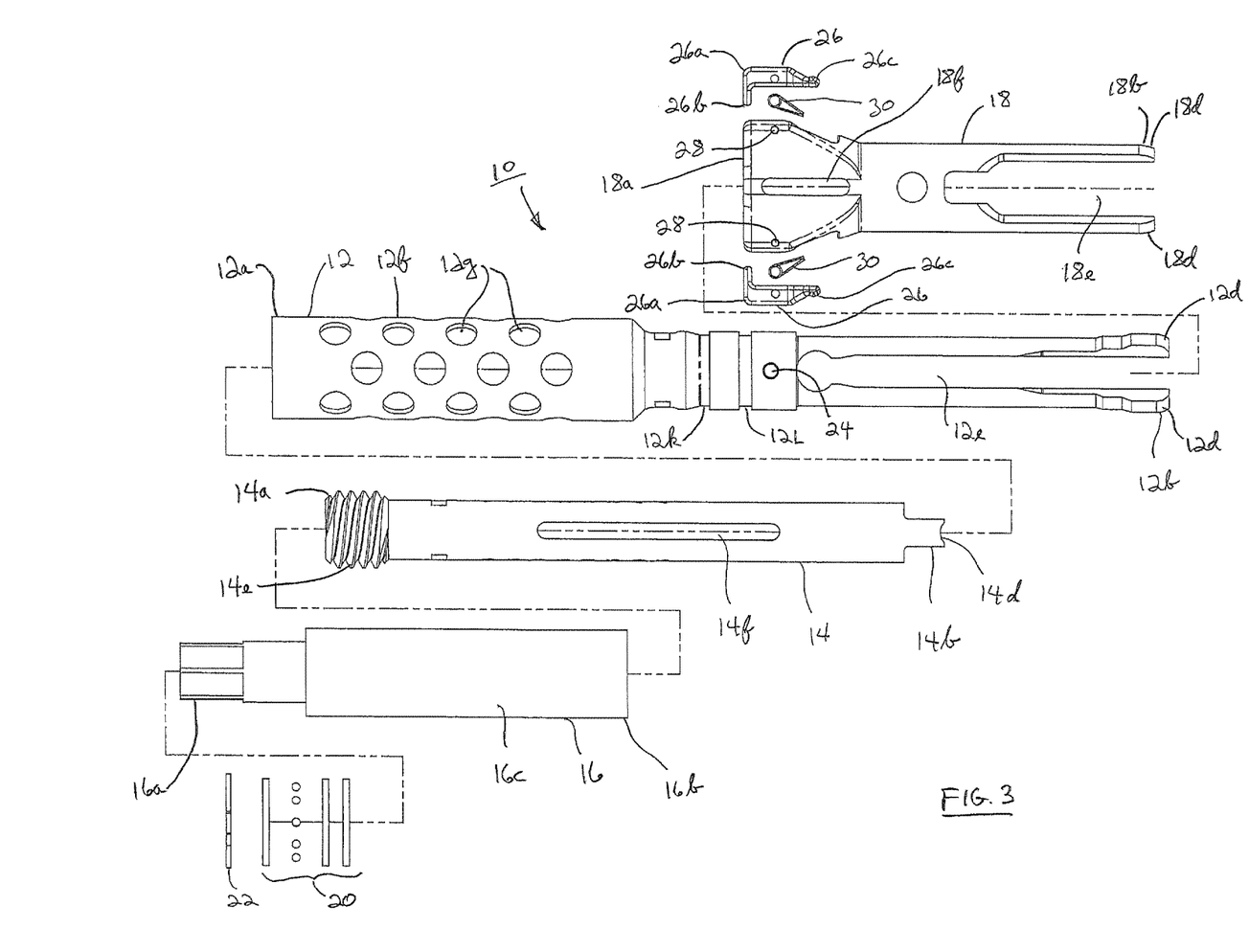
FIG. 3 is an exploded view of the rod reducer of FIG. 1.

Turning now to FIGS. 1-3 a spinal rod reducer 10 in accordance with a particular arrangement of the subject invention is shown. Rod reducer 10 comprises an elongate tubular body 12, a threaded rod reduction member 14, a threaded rotatable reduction knob 16, and a locking sleeve 18. Tubular body 12 has a proximal end 12a and a distal end 12*b* and a lumen 12*c* extending therethrough. A pair of spaced, flexible anchor attachment members 12*d* is disposed adjacent distal end 12*b* of tubular body 12, anchor attachment members 12*d* defining therebetween a slot 12*e* opening at the distal end 12*b* and extending for a length proximally. Attachment members 12*d* are configured to engage a bone anchor, such as a pedicle screw, in a manner to align slot 12*e* with the U-shaped rod receiving opening of the bone anchor. Tubular body 12 has an enlarged portion 12*f* adjacent proximal end 12*a*, enlarged portion 12*f* serving as a handle for rod reducer 10 and including in a particular arrangement a plurality of openings 12*g* to assist the user in grasping rod reducer 10. Between proximal end 12*a* and distal end 12*b* tubular body 12 has at least one window 12*h* extending therethrough in communication with lumen 12*c*. In a particular arrangement, a second window 12*h* is provided on the opposite side of tubular body 12. The purpose of windows 12*h* will be described hereinafter.

Threaded rod reduction member 14, as illustrated in FIGS. 1-3, has a proximal end 14*a* and a distal end 14*b*, and is supported by tubular body 12 for axial movement within tubular body lumen 12*c*, as will be described. In a particular arrangement, rod reduction member 14 is a generally cylindrical inner tube having a central lumen 14*c*. Distal end 14*b* of rod reduction member 14 includes a rod contacting surface 14*d* for engaging a spinal fixation rod to urge such rod into the rod-receiving opening of the bone anchor upon movement of rod reduction member 14 distally, as will be described. Rod contacting surface 14*d* may include a curved indentation, as shown in FIG. 3, to substantially conform to the curvature of the spinal rod to assist in the reduction process. In the particular arrangement where rod reduction member is tubular, rod contacting surface 14*d* may be defined by a pair of diametrically spaced portions that together engage a spinal fixation rod at two axially spaced locations along the rod axis during rod reduction.

As illustrated particularly in FIGS. 2-3, rod reduction member 14 includes exterior threads 14*e* at proximal end 14*a*. Rod reduction member 14 includes an elongated slot 14*f* extending therethrough in communication with lumen 14*c*, the purpose of which will be described. Rod reduction member 14 includes thereon a first series of spaced indicia 14*g* that are axially spaced to individually align with at least one window 12*h* upon axial movement of rod reduction member 14 within lumen 12*c* of tubular body 12. Each individual indicia 14*g* is representative of a distance a spinal fixation rod is to be reduced into the rod-reducing opening of the bone anchor, as will be described. In a particular arrangement, rod reduction member 14 may include a second series of such spaced indicia 14*g* on the opposite side, such second spaced indicia 14*g* being aligned axially with the first series of indicia 14*g* and being representative of the same distances as the first series of indicia 14*g*. The second series of spaced indicia 14*g* are also axially spaced to individually align with at the second window 12*h* upon axial movement of rod reduction member 14 within lumen 12*c* of tubular body 12. As such, the same representative distance would be displayed through both windows 12*h*.

Threaded rotatable reduction knob 16 as shown in FIGS. 1-3 has a proximal end 16*a* and a distal end 16*b*. Reduction knob 16 in a particular arrangement is generally cylindrical having an outer surface 16*c*, an inner surface 16*d* and a central lumen 16*e* extending therethrough. Inner surface 16*d* comprises interior threads 16*f* configured to be in threaded engagement with exterior threads 14*e* of rod reduction member 14, as depicted in FIG. 2. Reduction knob 16 is further configured to reside within enlarged portion 12*f* of tubular body 12 such that distal end 16*b* engages a transverse shoulder 12*i* within lumen 12*c* of tubular body 12, as illustrated in FIG. 2. This prevents reduction knob 16 from moving axially distally relative to tubular body 12. Adjacent proximal end 16*a*, reduction knob 16 is contained within tubular body 12 by a thrust bearing 20 and a locking clip 22. Locking clip 22 is supported within an interior groove 12*j* at the proximal end 12*a* of tubular body 12. Locking clip 22 prevents reduction knob 16 from moving axially proximally relative to tubular body 12. Thrust bearing 20 allows reduction knob 16 to rotate within lumen 12*c* of tubular body 12. Therefore, while reduction knob 16 can rotate while not moving axially, rod reduction member 14 is keyed to tubular body 12, as will be described, to move axially but not rotationally. As such, as a result of the threaded connection between threads 14*e*/16*f* of rod reduction member and reduction knob 16, respectively, rotation of reduction knob 16 will axially move rod reduction member 14 within tubular body 12. Reduction knob 16 includes a tool engagement portion 16*g* extending outwardly beyond proximal end 12*a* of tubular body 12, tool engagement portion 16*g* being configured to mate with a tool (not shown) for applying a rotational force to reduction knob 16.

Details of locking sleeve 18 are now described with respect to FIGS. 2-3. Locking sleeve 18 has a proximal end 18*a*, a distal end 18*b* and a lumen 18*c* extending therethrough. A pair of spaced locking members 18*d* is disposed adjacent distal end 18*b* of locking sleeve 18, locking members 18*d* defining therebetween a channel 18*e* opening at the distal end 18*b* and extending for a length proximally. Locking sleeve 18 is slidably supported for axial but not rotational movement on distal end 12*b* of tubular body 12. Such axial movement of locking sleeve 18 is independent of any movement of rod reduction member 14. During such axial movement locking sleeve channel 18*e* is aligned with tubular body slot 12*e* as locking sleeve 18 is axially moved from a first position to a second position, as will be described. Locking sleeve 18 includes an elongated slot 18*f* extending therethrough in communication with lumen 18*c*. A pair of pins 24, supported by tubular body 12 and extending generally diametrically oppositely outwardly from tubular body 12, communicates with rod reduction member lumen 14*c* and reduction knob lumen 16*c*. Pins 24 are received in locking sleeve elongated slot 18*f*, allowing a limited amount of axial movement of locking sleeve 18 relative to tubular body 12 while preventing relative rotational movement therebetween. Similarly pins 24 are received in rod reduction member elongated slot 14*f*, allowing a limited amount of axial movement of rod reduction member 14 relative to tubular body 12 while preventing relative rotational movement therebetween. As such, both locking sleeve 18 and rod reduction member 14 are keyed to tubular body by pins 24.

Referring still to FIGS. 1-3, locking sleeve 18 includes a pair of locking elements 26 supported generally diametrically oppositely at the proximal end 18*a* of locking sleeve 18. In a particular arrangement, each locking element 26 comprises a spring-loaded latch 26*a* that is supported by a pin 28 for pivotal movement thereon. A torsion spring 30 may be provided in association with each pin 28 and latch 26*a* to bias each latch 26*a* toward tubular body 12, as will be described. Each latch 26*a* has at one end a contact portion 26*b* configured to engage a portion of tubular body 12, such as cavities 12*k* and 12L formed into the wall of tubular body 12, as shown in FIGS. 2 and 3. Cavities 12*k* and 12L in a particular arrangement are axially spaced grooves formed circumferentially around tubular body 12. Cavity 12*k* is engaged by spring latch contact portion 26*b* when locking sleeve 18 is in the first position, and cavity 12L is engaged by spring latch contact portion 26b when locking sleeve 18 is in the other position, as will be described. The other end of each latch 26a includes a projecting button 26c that may be manually depressed in a manner to overcome the bias force provided by torsion spring 30. While a pair of locking elements 26 is described it should be appreciated that a single locking element 26 or more than two locking elements 26 may be used.

Figure 4:
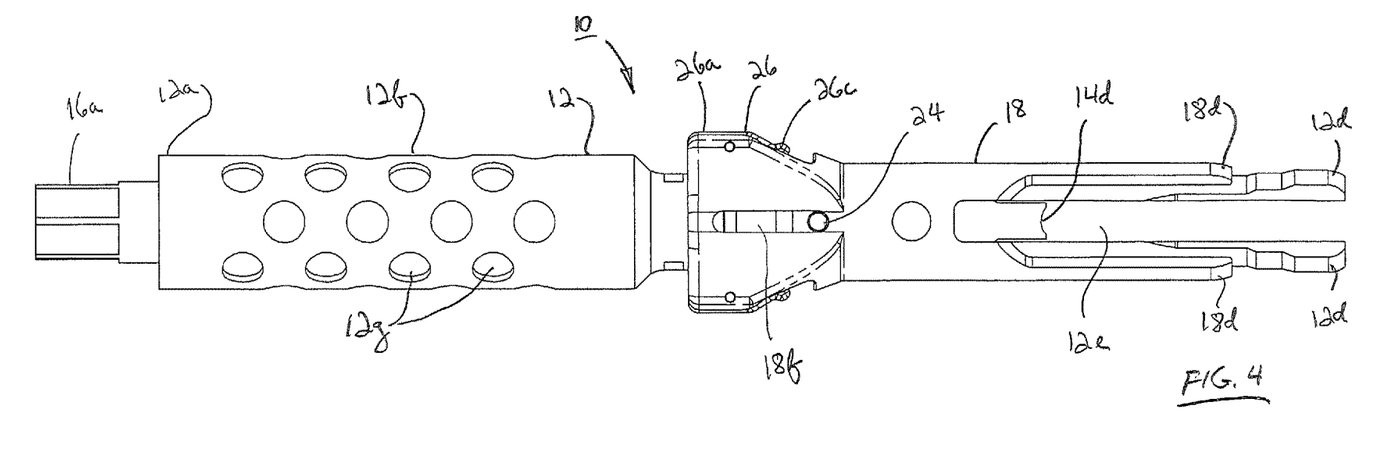
FIG. 4 is a top plan view of the rod reducer of FIG. 1 with the locking sleeve located in a first position allowing attachment to a bone anchor.
Figure 5:
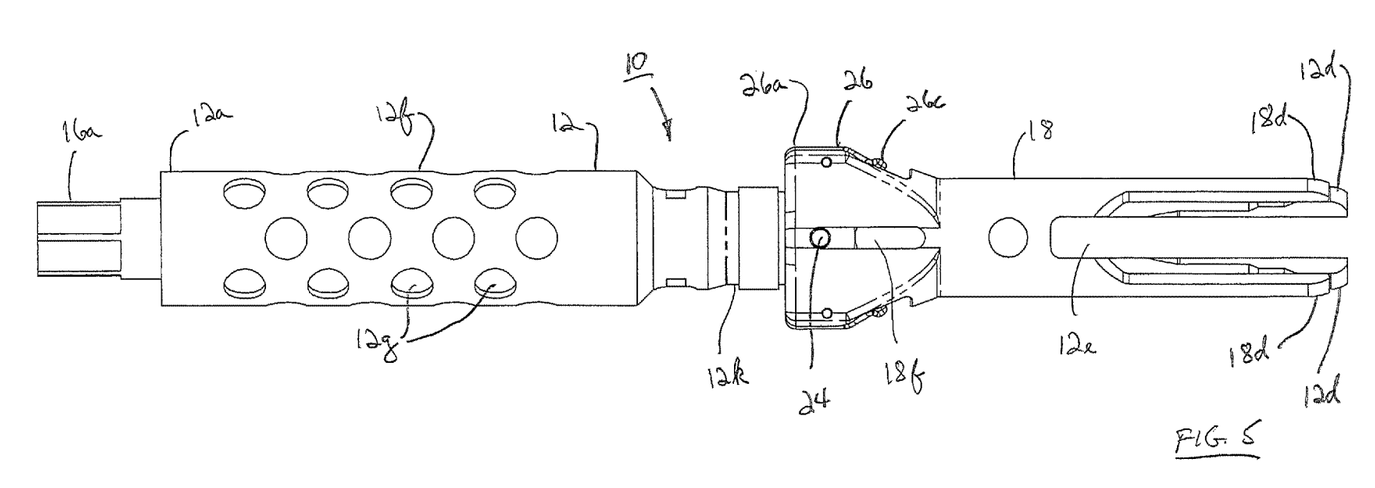
FIG. 5 is a view of the rod reducer of FIG. 4 with the locking sleeve moved to a second position for secure attachment to a bone anchor.

As shown in FIG. 4, locking sleeve 18 is shown in the first position relative to tubular body 12. In this first position, spring latch contact portions 26b are biased into engagement with tubular body cavities 12k by torsion spring 30. As such, locking sleeve 18 is releasably secured in this fixed axial first position relative to tubular body 12. In this first position, locking sleeve locking members 18d are spaced axially proximally of and thereby exert minimal radial constraints on tubular body anchor attachment members 12d, allowing anchor attachment members 12d to flexibly snap onto a bone anchor, such as the yoke of a pedicle screw. In this first position, pin 24 is situated at the distalmost location within locking sleeve elongated slot 18f. Depression of spring latch buttons 26c in a manner to overcome the bias force of torsion spring 30 allows contact portions 26b to be pivotally released from cavities 12k thereby allowing locking sleeve 18 to move axially distally to the second position, as shown in FIG. 5. In this second position, locking sleeve locking members 18d substantially cover and thereby radially constrain movement of anchor members 12d to form a secure attachment between anchor members 12d and the bone anchor. In the second position spring latch contact portions 26b are moved to cavities 12L (as shown in FIG. 2), thereby releasably securing locking sleeve 18 relative to tubular body 12 under the bias provided by torsion spring 30. In this second position, pin 24 is situated at the proximalmost location within locking sleeve elongated slot 18f, as depicted in FIG. 5.

Having described the details of threaded rod reducer 10, the use thereof in a surgical procedure is now described. Once a desired number of bone anchors, such as pedicle screws, are suitably attached to vertebrae of a spine the spinal fixation rod must be nestled or seated within the U-shaped rod-receiving opening of the pedicle screw yoke, as noted hereinabove. The rod reducer 10 of the subject invention may be attached to the pedicle screw yoke either before the fixation rod is introduced to the surgical site or after the fixation rod is placed into the pedicle screw yokes but not fully reduced. In the first instance of use, the arms of the yoke defining the U-shaped opening may serve as a guide to initially introduce the fixation rod, while in the second instance of use slot 12e of the rod reducer tubular body 12 may serve as the rod introduction guide.

Figure 6A:
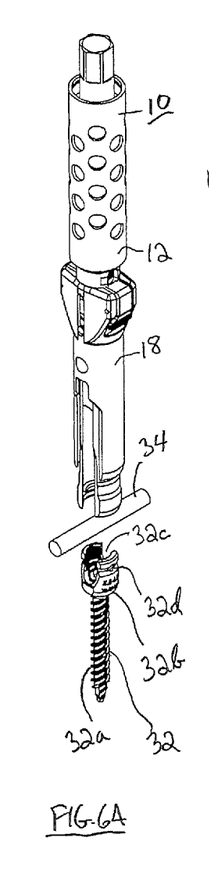
FIGS. 6A-G show a sequence of steps for use of the rod reducer of FIG. 1 in a spinal surgical procedure.
Figure 6B:
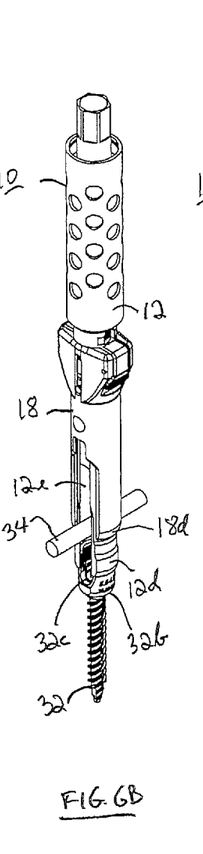
Figure 6C:
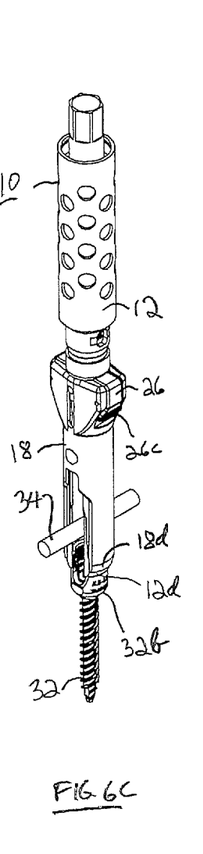
Figure 6D:
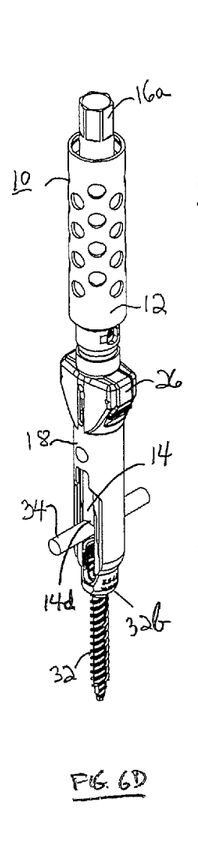

The sequence of the steps of using rod reducer 10 in a spinal surgical procedure, such as in an open or mini open approach, is illustrated FIGS. 6A-G. FIG. 6A shows a pedicle screw 32 having a threaded shaft 32a and a yoke 32b having a U-shaped rod-receiving opening 32c. Yoke 32b may have an external groove 32d for releasable attachment to reducer 10. Pedicle screws 32 may be monoaxial or polyaxial, such as those described hereinabove. An elongated spinal fixation rod 34 is shown in position slightly above pedicle screw 32 with threaded rod reducer 10 positioned above rod 34 in the loading position and ready for reducing rod 34 into rod-receiving opening 32c. At this time, locking sleeve 18 of rod reducer 10 is in the first position as shown in FIG. 4 whereby anchor attachment members 12b are not constrained and are capable of flexing. In FIG. 6B rod reducer 10 is flexibly attached to pedicle screw 32 by snapping flexible anchor attachment members 12d into groove 32d of yoke 32b so that the rod-receiving opening 32d of pedicle screw 32 is aligned and parallel with tubular body slot 12e of reducer 10.

With rod reducer 10 attached to pedicle screw yoke 32b, both locking element buttons 26c are squeezed to release the contact between locking elements 26 and tubular body 12. Sleeve 18 is then manually pulled distally to the second position shown in FIG. 6C. In this second position locking sleeve locking members 18d overlap anchor members 12d, radially constraining movement of anchor members 12d and providing a secure attachment between anchor members 12d and pedicle screw 32 by maintaining anchor members 12d in engagement with yoke groove 32d. The secure attachment in the second position is maintained as latch contact portions 26b reside in cavities 12L (as shown in FIG. 2) under the bias provided by torsion spring 30.

At this point, the desired amount of rod reduction can be determined and set. The amount of reduction can be read through at least window 12h on one side of the reducer 10, as shown in FIG. 1. To achieve movement of the rod reduction member 14 distally and rod reduction, reduction knob 16 is turned counterclockwise until rod contacting surface 14d contacts fixation rod 34. Rotation of reduction knob 16 may be effected by attaching a suitable tool such as a wrench (not shown) to engagement portion 16a. The desired amount of reduction may be within a range of, for example, 0 and 45 mm for lumbar spine procedures. Depending upon the application, such as in other sections of the spine, other suitable reduction ranges may apply. As a result of axial movement of rod reduction member 14, one of indicia 14g spaced axially thereon will move into alignment with window 12h for display, as illustrated in FIG. 1, thereby providing a visual indication to the surgeon of the amount of reduction that would be effected. In the arrangement where a second window 12h and a second series of indicia 14g are provided, the amount of rod reduction may be read on either side of rod reducer 10.

Figure 6E:
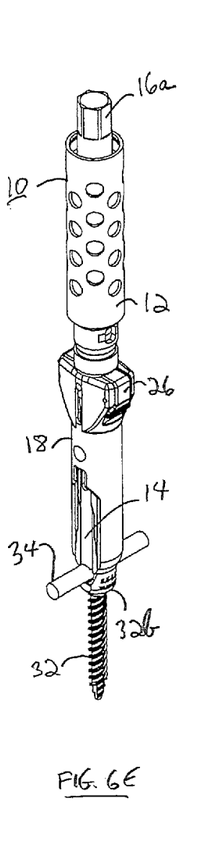
Figure 6F:
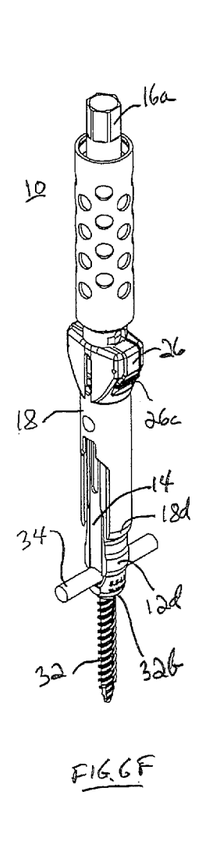
Figure 6G:
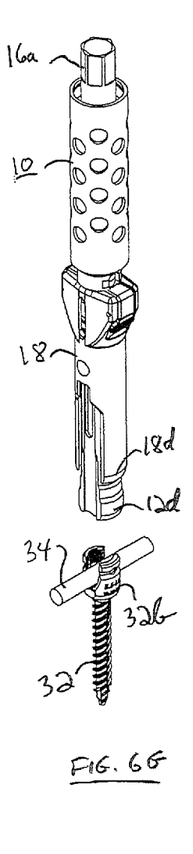

Further rotation of reduction knob 16 counterclockwise causes rod reduction member 14 to push down distally on fixation rod 34 and pull up on yoke 32b as shown in FIG. 6E, thereby persuading fixation rod 34 towards yoke 32b and reducing rod 34 to yoke 32b and the vertebral body to which pedicle screw 32 is attached. A locking member in the form of a set screw may then be passed through tubular body lumen 12c of rod reducer 10 to provisionally lock rod 34 into pedicle screw 32. Once rod 34 is locked into yoke 32b, rod reducer 10 may be disengaged from yoke 32b by depressing the two buttons 26c on locking sleeve 18 while simultaneously sliding locking sleeve 18 towards the proximal end of reducer 10 as shown in FIG. 6F. Anchor attachment members 12b of reducer 10 will flexibly splay outwardly, allowing reducer 10 to be separated from yoke 32b as illustrated in FIG. 6G. It should be appreciated that rod reduction member 14 does not need to be retracted prior to removal of reducer 10 from pedicle screw 32. Optionally, a surgeon may choose, however, to first retract rod reduction member 14 prior to separating rod reducer 10 from pedicle screw 32 by clockwise rotation of reduction knob 16 to thereby move reduction member 14 proximally relative to tubular body 12.

Having described the construction and operation of rod reducer 10, it should be understood that there are a number of particularly desirable features of this first embodiment. For example, in one aspect of rod reducer 10, there is independent movement of the rod reduction member and the locking sleeve. This allows the rod reducer to be attached to a pedicle screw separate from the process of rod reduction either before or after the rod is inserted. This feature also allows the rod reducer to be removed from the pedicle screw after rod reduction without withdrawing the rod reduction member, thereby saving the surgeon time to complete the procedure.

In another aspect of the rod reducer 10, the user can determine and set how much rod reduction is desired prior to attaching the instrument.

Turning now to FIGS. 7-12G, a rod reducer 110 in accordance with a second embodiment of the invention is described. As with the first embodiment of rod reducer 10, rod reducer 110 is configured for reducing a spinal rod 34 into a rod-receiving opening 32c of a bone anchor 32, as shown in FIG. 12A. FIGS. 12A-G illustrate the sequence of operation of the rod reducer 110, as will be further described.

Figure 7:
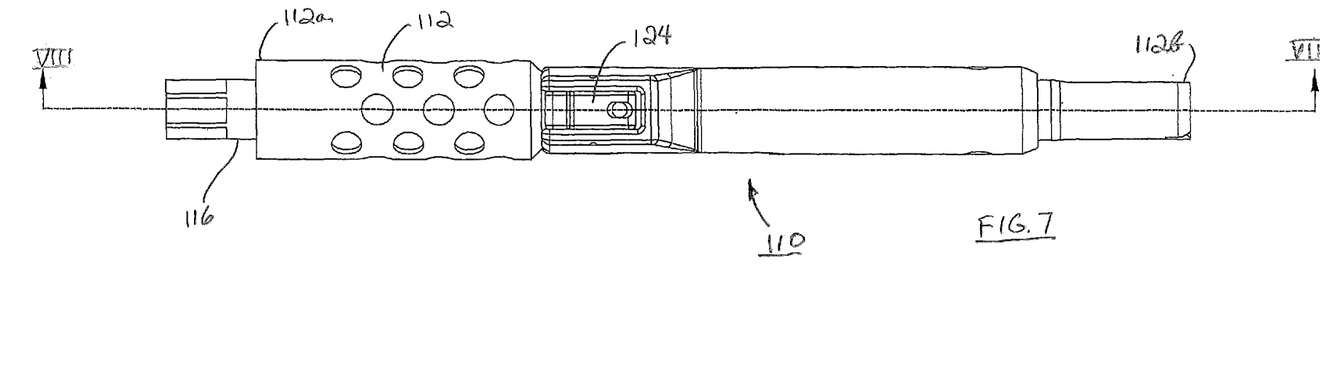
FIG. 7 is a side elevation view of a threaded rod reducer for use during spinal surgery in accordance with a second embodiment of the present invention.
Figure 8:
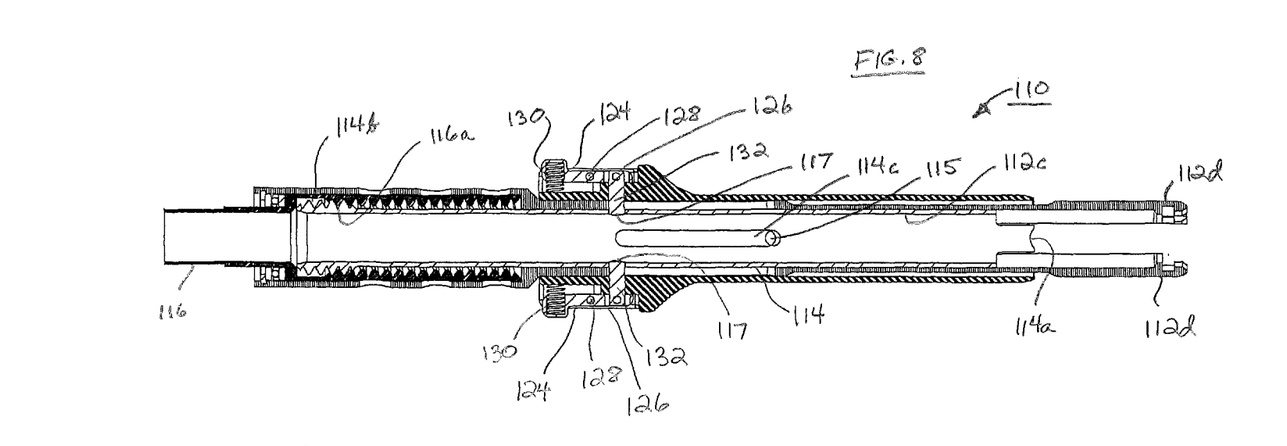
FIG. 8 is a longitudinal cross-sectional view of the rod reducer as seen along viewing lines VIII-VIII of FIG. 7.

Rod reducer 110, as detailed in FIGS. 7-9, comprises an elongate tubular body 112 having a proximal end 112a, a distal end 112b, and lumen 112c extending therethrough. A pair of spaced, flexible anchor attachment members 112d are formed at the distal end 112b of the tubular body 112. A slot 113 extends through distal end 112b for an extent toward proximal end 112a. Slot 113 has a first portion 113a adjacent distal end 112b and a second portion 113b extending more proximally. The width of first slot portion 113a is greater than the width of second slot portion 113b. An inclined transition surface 113c joins first slot portion 113a and second slot portion 113b. A pair of oppositely spaced pins 115 are supported by tubular body 112 for interaction with a rod reduction member 114 and a locking sleeve 118, as will be described. In the normal position shown in FIG. 8 attachment members 112d are parallel to each other but may be flexed elastically radially outwardly upon manual attachment of rod reducer 110 to the bone anchor 32. Tubular body 112 has at least one window 112e extending therethrough in communication with lumen 112c. In a particular arrangement, a second window 112e is provided on the opposite side of tubular body 112. The purpose of windows 112e will be described hereinafter A threaded rod reduction member 114 having a rod contacting surface 114a at its distal end is supported for axial but not rotational movement within the lumen 112c of the tubular body 112. Rod reduction member 114 includes external threads 114b at its proximal end. An elongated slot 114c extends through rod reduction member 114 for receipt of pin 115, the length of elongated slot 114c limiting the translational movement of rod reduction member 114 within tubular body 112 while the width of slot 114c substantially prevents relative rotational movement therebetween. A pair of oppositely spaced grooves 117 defining pin engagement surfaces are formed into the rod reduction member 114 adjacent threads 114b, as shown in FIG. 8. Rod reduction member 114 includes thereon a first series of spaced indicia 114d that are axially spaced to individually align with at least one window 112e upon axial movement of rod reduction member 114 within lumen 112c of tubular body 112.

A reduction knob 116 is supported for rotational but not translational movement within lumen 112c adjacent the proximal end 112a of tubular body 112 in a manner similar to reduction rod 116 of the first embodiment and is similarly contained within tubular body 112 by a thrust bearing 120 and a locking clip 122. Reduction knob 116 includes internal threads 116a for threaded engagement with the external threads 114b of rod reduction member 114. Rotation of reduction knob 116 may be effected by attaching a suitable tool such as a wrench to engagement portion 116a at the proximal end of reduction knob 116.

A locking sleeve 118 is supported for slidable axial movement on the exterior surface of tubular body 112 to fixedly secure the attachment members 112d to the bone anchor 32. An elongated slot 118a as shown in FIG. 9 extends through locking sleeve 118 for receipt of pin 115, the length of elongated slot 118a limiting the translational movement of locking sleeve 118 on tubular body 112. Locking sleeve 118 supports a pair of release pins 119 adjacent the distal end of locking sleeve 118. The diameter of each release pin 119 is slightly less than the width of slot first portion 113a for free sliding movement therewithin, but greater than the width of slot second portion 113b. Locking sleeve 118 supports a pair of oppositely disposed, spring-loaded buttons 24 that serve as locking elements to selectively couple rod reduction member 114 and locking sleeve 118. Each button 124 comprises a spring-loaded arm 126 that is pivotally supported at a pivot point 128 for pivotal movement thereabout. A compression spring 130 may be provided in association with each arm 126 to bias each arm 126 toward tubular body 112. Each button 124 supports a pin 132 that is radially outwardly movable upon depression of each button 124 to allow selective coupling of locking sleeve 118 to rod reduction member 114. Each pin 132 defines a contact portion that is dimensioned to be received within a respective groove 117 of rod reduction member 114, as shown in FIG. 8.

Figure 10:
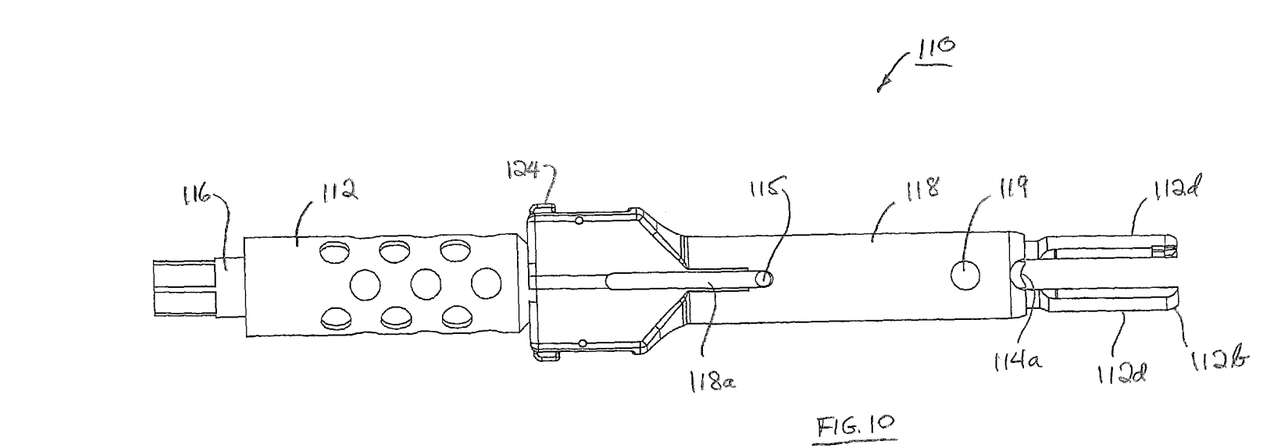
FIG. 10 is a top plan view of the rod reducer of FIG. 7 with the locking sleeve located in a first position allowing attachment to a bone anchor.
Figure 11:
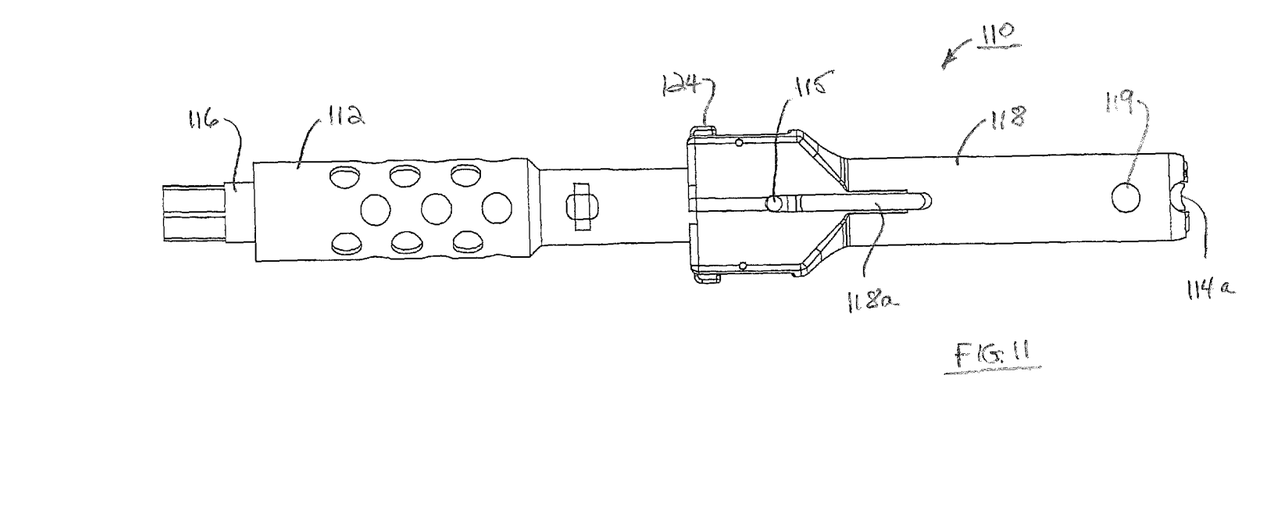
FIG. 11 is a view of the rod reducer of FIG. 10 with the locking sleeve moved to a second position for secure attachment to a bone anchor.
Figure 12A:
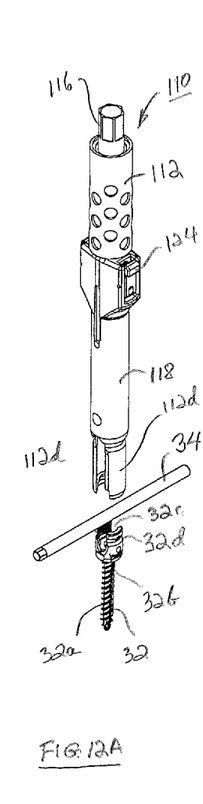
FIGS. 12A-G show a sequence of steps for use of the rod reducer of FIG. 7 in a spinal surgical procedure.
Figure 12B:
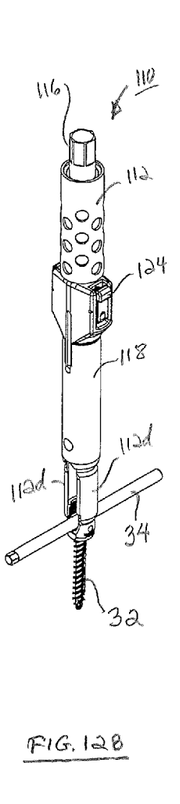
Figure 12C:
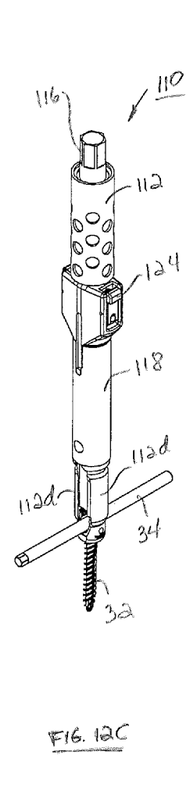
Figure 12D:
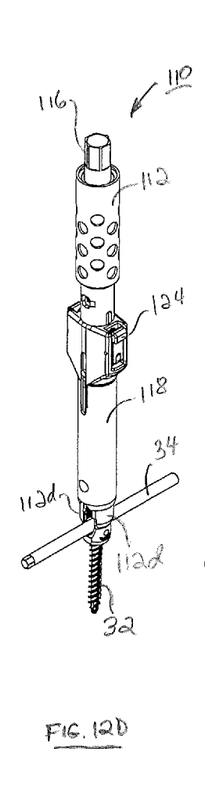

In use, rod reducer 110 is initially in the position shown in FIG. 10. In this position locking sleeve 118 is proximally withdrawn from anchor attachment members 112d, release pin 119 is disposed within slot first portion 113a and the pins 132 of buttons 124 are disposed within respective opposite grooves 117. Anchor attachment members 112d are parallel to each other while rod contacting surface 114a is disposed proximally of distal end 112b of tubular body 112 and between anchor attachment members 112d. In this position rod reducer 110 is attached to bone anchor 32 as shown in FIG. 12B. Anchor attachment members 112d are manually introduced over the rod receiving yoke 32b of the bone anchor 32 and are then snapped onto the exterior of the bone anchor 32. During this manual process, attachment members 112d temporarily flex radially outwardly and thereafter elastically return to the normal parallel position upon attachment. As such, the attachment is not effected in any manner by the movement of locking sleeve 118 or rotation of reduction knob 116. Once attached to bone anchor 32 shown in FIG. 12C, buttons 124 on locking sleeve 118 are depressed in a first mode to separate pins 132 from groves 117 to thereby decouple locking sleeve 118 from rod reduction member 114. Upon detachment, locking sleeve 118 is manually moved distally independently of movement of rod reduction member 114 to slide over and exteriorly engage at least an axial portion of attachment members 112d as shown in FIG. 12D to secure the connection of the attachment members 112d to bone anchor 32 and to prevent outward radial splaying of attachment members 112d that could inadvertently cause separation of rod reducer 110 from bone anchor 32.

Figure 12E:
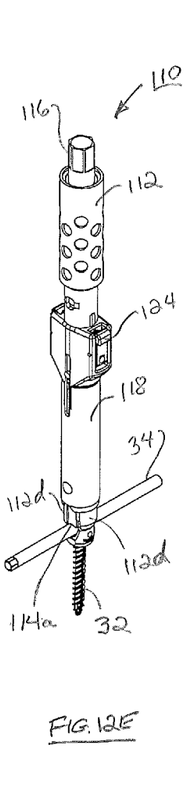
Figure 12F:
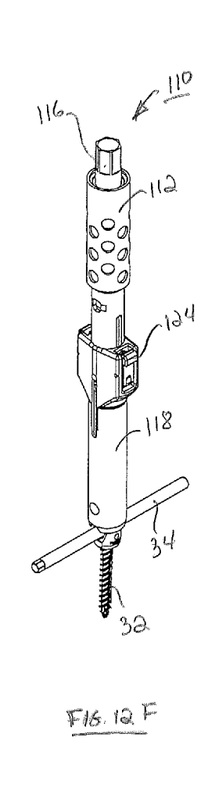

Upon attachment of rod reducer 110 to bone anchor 32 and securement of attachment members 112d by locking sleeve 118, reduction knob 116 is rotated to cause axial distal movement of rod reduction member 114. Rotation of reduction knob 16 causes only axial translational movement of rod reduction member 114 and rod contacting surface 114a at the distal end thereof. Such distal movement of rod reduction member 114 will cause rod contacting surface 114a to engage the spinal rod 34 as shown in FIG. 12E and to urge such rod 34 into the yoke 32b of bone anchor 32. For an extent of such distal movement, rod reduction member 114 will move axially distally independently of locking sleeve 118 which will remain in the position shown in FIG. 12D as initially manually placed around attachment members 112d. Upon further axial distal movement of rod reduction member 114 relative to tubular body 112, pins 132 on button 124 will axially align with grooves 117 in a second mode thereby reengaging with grooves 117 and re-coupling locking sleeve 118 with rod reduction member 114. Further rotation of reduction knob 116 will then cause joint distal movement of rod reduction member 114 and locking sleeve 118 relative to tubular body 112 to the position shown in FIGS. 11 and 12F to properly seat rod 34 into yoke 32b of bone anchor 32.

This will assure that locking sleeve 118 substantially fully covers anchor attachment members 112d and maintains the attachment of rod reducer 110 to bone anchor 32 during the entire rod reduction process.

Figure 12G:
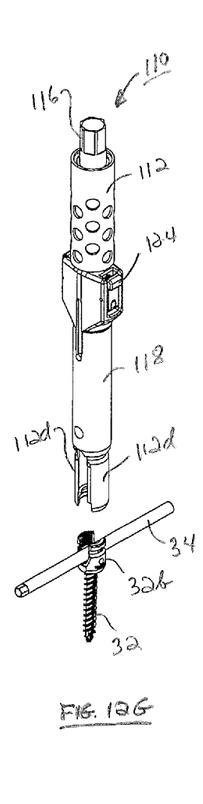

Upon completion of proper rod reduction, buttons 124 are again depressed to decouple locking sleeve 118 from rod reduction member 114. Once decoupled, locking sleeve 118 is manually slid proximally along tubular body 112 until release pin 119 engages the inclined surfaces 113c at the transition of the first and second slot portions 113a and 113b. Since the diameter of release pin 119 is greater than the narrower second slot portion 113b proximal movement of release pins 119 against inclined surfaces 113c will cause anchor attachment members 112d to elastically flex radially outwardly to separate rod reducer 110 from bone anchor 32 as shown in FIG. 12G. In this position, rod reducer 110 may be removed from the surgical site. Release of manual force from the locking sleeve 118 will cause release pins 119 to move back into the wider first slot portion 113a while pins 132 of buttons 124 reestablish connection with grooves 117 with rod reducer 110 again being in the position of FIG. 10.

It should therefore be understood that while various aspects of the invention have been presented herein, various changes, modifications and further applications may be made without departing from the spirit of the invention and the scope of the appended claims.

What is claimed is:

1. A spinal rod reducer for reducing a spinal rod into a rod-receiving opening of a bone anchor, comprising:
   an elongate tubular body having a proximal end, a distal end and a lumen extending therethrough, and a pair of spaced flexible anchor attachment members adjacent the distal end of said tubular body, said spaced attachment members defining a slot therebetween, the distal end of said attachment members being configured to engage said bone anchor in a manner to align said slot with said rod-receiving opening of said bone anchor, at least one pin supported by said tubular body, said at least one pin extending transversely outwardly from said tubular body;
   a threaded rod reduction member supported for axial movement within said lumen of said tubular body, said rod reduction member including a rod contacting surface movable to a position between said attachment members, wherein said rod reduction member has an axially extending elongated slot in receipt of said at least one pin for preventing rotational movement of said rod reduction member relative to said tubular body;
   a threaded rotatable reduction knob threadably engaged with said reduction rod member, rotation of said reduction knob causing said rod reduction member to move axially relative to said tubular body and thereby move said rod contacting surface within said slot between said attachment members; and
   a locking sleeve supported for axial movement on said tubular body, said locking sleeve being configured to slide over and exteriorly engage said attachment members during said axial movement, said locking sleeve including a locking element for selectively releasably coupling said locking sleeve and said rod reduction member, such that in a first mode said locking sleeve is decoupled from said rod reduction member to allow axial movement independently of movement of said rod reduction member relative to said tubular body, and in a second mode such that said locking sleeve is coupled to said rod reduction member for axial movement jointly therewith relative to said tubular body, wherein said locking sleeve has an axially extending elongated slot in receipt of said at least one pin for limiting the axial movement of said locking sleeve.

2. The spinal rod reducer of claim 1, wherein said reduction knob is attached to the proximal end of said tubular body within said lumen in a manner to allow rotational but not axial movement relative to said tubular body.

3. The spinal rod reducer of claim 2, wherein said reduction knob is generally cylindrical having an outer surface and an inner surface, said inner surface including threads.

4. The spinal rod reducer of claim 3, wherein said rod reduction member is generally cylindrical having a distal end and a proximal end, said rod contacting surface being disposed at said distal end, said proximal end having exterior threads in threaded engagement with the threads on the inner surface of said reduction knob.

5. The spinal rod reducer of claim 1, wherein said locking element comprises a spring-loaded button pivotally supported exteriorly on said locking sleeve, said button having a contact portion configured to releasably engage an engagement surface on said rod reduction member.

6. The spinal rod reducer of claim 5, wherein said spinal rod reducer comprises a pair of spring-loaded buttons disposed oppositely on said locking sleeve, each spring-loaded button comprising a compression spring to bias each locking element toward said tubular body in releasable engagement.

7. The spinal rod reducer of claim 5, wherein said locking element is depressible in said first mode to separate and thereby decouple said button contact portion from said engagement surface on said rod reduction member to thereby allow said independent axial movement of said locking sleeve on said tubular body relative to said rod reduction member.

8. The spinal rod reducer of claim 7, wherein said button contact portion and said engagement surface on said rod reduction member are configured such that upon axial distal movement of said rod reduction member relative to locking sleeve and said tubular body, said rod reduction member engagement surface will axially align with said contact portion of said button causing said contact portion and said engagement surface to recouple in said second mode and thereby allow said joint movement of said locking sleeve and said rod reduction member relative to said tubular body.

9. The spinal rod reducer of claim 8, wherein said locking element comprises a pair of said spring-loaded buttons, said buttons being disposed approximately oppositely on the exterior of said locking sleeve.

10. The spinal rod reducer of claim 1, wherein said tubular body has a window exposing a portion of said rod reduction member.

11. The spinal rod reducer of claim 10, wherein said rod reduction member includes thereon a series of spaced indicia that individually align with said window upon axial movement of said rod reduction member within the lumen of said tubular body, each individual indicia being representative of a distance said spinal rod is reduced into said rod-reducing opening of said bone anchor.

12. The spinal rod reducer of claim 1, wherein said reduction knob includes a tool engagement portion extending outwardly beyond the proximal end of said tubular body, the tool engagement portion being configured to mate with a tool for applying a rotational force to said reduction knob.

13. The rod spinal reducer of claim 1, wherein said slot of said tubular body has a first portion adjacent said distal end and a second portion extending more proximally of said slot first portion, said slot first portion having a width greater than a width of said second slot portion, said slot first portion and said slot second portion being joined by an inclined transition surface.

14. The spinal rod reducer of claim 13, wherein said locking sleeve supports at least one release pin adjacent said distal end of said locking sleeve, said release pin having a dimension slightly less than the width of said slot first portion for free sliding movement therewithin and greater than the width of said slot second portion, proximal movement of said locking sleeve relative to said tubular body causing said release pin to move against said inclined transition to thereby cause said anchor attachment members to elastically flex radially outwardly such that said rod reducer may be removed from the surgical site.

15. A spinal rod reducer for reducing a spinal rod into a rod-receiving opening of a bone anchor, comprising:
an elongate tubular body having a proximal end, a distal end and a lumen extending therethrough, and a pair of spaced flexible anchor attachment members adjacent the distal end of said tubular body, said spaced attachment members defining a slot therebetween, the distal end of said attachment members being configured to engage said bone anchor in a manner to align said slot with said rod-receiving opening of said bone anchor, at least one pin supported by said tubular body, said at least one pin extending transversely outwardly from said tubular body;
a rod reduction member supported for axial movement within said lumen, said rod reduction member including a rod contacting surface movable to a position between said attachment members, wherein said rod reduction member has an axially extending elongated slot in receipt of said at least one pin for preventing rotational movement of said rod reduction member relative to said tubular body;
a locking sleeve supported for axial movement on said tubular body, said locking sleeve being configured to slidably engage said attachment members during said axial movement of said locking sleeve, said locking sleeve including a locking element for releasably securing said locking sleeve in a fixed axial position relative to said tubular body attachment members wherein said locking sleeve has an axially extending elongated slot in receipt of said at least one pin for limiting the axial movement of said locking sleeve;
a reduction knob supported for rotational movement within said lumen and cooperatively engaged with said reduction rod member, rotation of said reduction knob causing said rod reduction member to move axially relative to said tubular body and thereby move said rod contacting surface within said slot between said attachment members, movement of said rod reduction member being independent of movement of said locking sleeve.

16. The spinal rod reducer of claim 15, wherein said reduction knob is attached to the proximal end of said tubular body within said lumen in a manner to allow rotational but not axial movement relative to said tubular body.

17. The spinal rod reducer of claim 16, wherein said rod reduction member includes an outer surface having exterior threads and said reduction knob includes an inner surface having internal threads in threadable engagement with said exterior threads of said rod reduction member.

18. The spinal rod reducer of claim 17, wherein said rod reduction member has a distal end and a proximal end, said rod contacting surface being disposed at said distal end and said exterior threads being disposed at said proximal end.

19. The spinal rod reducer of claim 15, wherein said locking element comprises a spring-loaded latch pivotally supported exteriorly on said locking sleeve, said latch having a contact portion configured to releasably engage a portion of said tubular body.

20. The spinal rod reducer of claim 19, wherein said locking element comprises a pair of said spring-loaded latches, said latches being disposed oppositely on the exterior of said locking sleeve.

21. The spinal rod reducer of claim 15, wherein said tubular body has a window exposing a portion of said rod reduction member.

22. The spinal rod reducer of claim 21, wherein said rod reduction member includes thereon a series of spaced indicia that individually align with said window upon axial movement of said rod reduction member within the lumen of said tubular body, each individual indicia being representative of a distance said spinal rod is reduced into said rod-reducing opening of said bone anchor.

23. The spinal rod reducer of claim 15, wherein said reduction knob includes a tool engagement portion extending outwardly beyond the proximal end of said tubular body, the tool engagement portion being configured to mate with a tool for applying a rotational force to said reduction knob.

24. The spinal rod reducer of claim 15, wherein said locking sleeve includes a pair of spaced locking members defining a channel therebetween, said locking sleeve channel being aligned during axial movement of said locking sleeve with said slot defined between said attachment members.

* * * * *